(12) United States Patent
Melvin et al.

(10) Patent No.: US 7,918,004 B2
(45) Date of Patent: Apr. 5, 2011

(54) TAMPON APPLICATOR BARRELS HAVING GRIPPING STRUCTURES AND METHODS OF FORMING

(75) Inventors: Wayne D. Melvin, Felton, DE (US); Michael L. Miller, Dover, DE (US); Jamshid Rejai, Dover, DE (US); Van T. Pham, Dover, DE (US); Joseph S. Konrad, Dover, DE (US); Wojtek S. Drewnowski, Richmond, VA (US)

(73) Assignee: Playtex Products, Inc., Westport, CT (US)

( * ) Notice: Subject to any disclaimer, the term of this patent is extended or adjusted under 35 U.S.C. 154(b) by 1085 days.

(21) Appl. No.: 11/541,127

(22) Filed: Sep. 29, 2006

(65) Prior Publication Data
US 2008/0005884 A1 Jan. 10, 2008

Related U.S. Application Data

(62) Division of application No. 10/870,276, filed on Jun. 17, 2004, now Pat. No. 7,798,986.

(60) Provisional application No. 60/480,559, filed on Jun. 20, 2003, provisional application No. 60/484,375, filed on Jul. 2, 2003.

(51) Int. Cl.
*B23P 17/00* (2006.01)
(52) U.S. Cl. ............ 29/419.1; 29/457; 604/15; 264/312
(58) Field of Classification Search ............... 29/419.1, 29/457, 283.5; 604/14–18; 264/310, 312; 493/463, 464, 480, 160, 185
See application file for complete search history.

(56) References Cited

U.S. PATENT DOCUMENTS

| | | | | |
|---|---|---|---|---|
| 2,489,502 | A | | 11/1949 | Ruth .............................. 604/18 |
| 2,587,717 | A | | 3/1952 | Fourness ......................... 604/18 |
| 2,600,971 | A | * | 6/1952 | Collins et al. ................ 493/363 |
| 2,703,042 | A | * | 3/1955 | Goodwin ...................... 493/160 |
| 3,305,931 | A | * | 2/1967 | Kerr .................................. 33/556 |
| 3,628,533 | A | | 12/1971 | Loyer ............................. 604/14 |
| 3,762,413 | A | | 10/1973 | Hanke ............................ 604/15 |
| 3,895,634 | A | | 7/1975 | Berger et al. ................... 604/14 |
| 4,027,673 | A | | 6/1977 | Poncy et al. ................. 604/369 |
| 4,211,743 | A | * | 7/1980 | Nauta et al. ................... 264/284 |
| 4,453,925 | A | * | 6/1984 | Decker ........................... 604/14 |
| 4,676,773 | A | | 6/1987 | Sheldon ......................... 604/16 |

(Continued)

FOREIGN PATENT DOCUMENTS

CA 2488813 12/2003

(Continued)

OTHER PUBLICATIONS

Canadian Office Action dated Aug. 2, 2010 from corresponding Application No. 2,606,853.

(Continued)

*Primary Examiner* — David P Bryant
*Assistant Examiner* — Christopher M Koehler
(74) *Attorney, Agent, or Firm* — Ohlandt, Greeley, Ruggiero & Perle, L.L.P.

(57) ABSTRACT

A tampon applicator barrel including a cardboard tube having a first end and a second end and at least one gripping structure defined from the cardboard tube proximate the second end is provided. The cardboard tube has a wall thickness of between about 0.015 and about 0.020 inches, while the gripping structure has a height of up to about 0.035 inches.

18 Claims, 4 Drawing Sheets

U.S. PATENT DOCUMENTS

| | | | |
|---|---|---|---|
| 4,699,610 A | 10/1987 | Hanano et al. | 604/16 |
| 4,787,895 A | 11/1988 | Stokes et al. | 604/358 |
| 4,857,044 A | 8/1989 | Lennon | 604/14 |
| 4,900,299 A | 2/1990 | Webb | 604/11 |
| 4,973,302 A | 11/1990 | Armour et al. | 604/15 |
| 5,087,239 A | 2/1992 | Beastall et al. | 604/14 |
| 5,153,971 A | 10/1992 | Van Iten | 28/118 |
| 5,158,535 A | 10/1992 | Paul et al. | 604/15 |
| 5,267,953 A | 12/1993 | Paul et al. | 604/15 |
| 5,279,541 A | 1/1994 | Frayman et al. | 604/14 |
| 5,290,501 A | 3/1994 | Klesius | 264/322 |
| 5,330,421 A | 7/1994 | Tarr et al. | 604/18 |
| 5,346,468 A | 9/1994 | Campion et al. | 604/13 |
| 5,348,534 A | 9/1994 | Tamaszewski et al. | 604/14 |
| 5,389,067 A | 2/1995 | Rejai | 604/14 |
| 5,395,308 A | 3/1995 | Fox et al. | 604/15 |
| 5,437,628 A | 8/1995 | Fox et al. | 604/14 |
| 5,533,990 A | 7/1996 | Yeo | 604/363 |
| 5,554,108 A | 9/1996 | Browning et al. | 604/15 |
| 5,558,631 A | 9/1996 | Campion et al. | 604/13 |
| 5,599,293 A | 2/1997 | Orenga et al. | 604/16 |
| 5,702,553 A * | 12/1997 | Iskra et al. | 156/203 |
| 5,738,646 A | 4/1998 | Fox et al. | 604/15 |
| 5,800,377 A | 9/1998 | Campion et al. | 604/13 |
| 5,891,081 A | 4/1999 | McNelis et al. | 604/14 |
| 5,931,803 A | 8/1999 | Jackson | 604/15 |
| 5,964,741 A | 10/1999 | Moder et al. | 604/358 |
| 6,024,716 A | 2/2000 | Rejai | 604/14 |
| 6,045,526 A | 4/2000 | Jackson | 604/15 |
| 6,056,714 A | 5/2000 | McNelis et al. | 604/14 |
| 6,095,998 A | 8/2000 | Osborn, III et al. | 604/11 |
| 6,179,802 B1 | 1/2001 | Jackson | 604/15 |
| 6,217,542 B1 | 4/2001 | Stevens et al. | 604/17 |
| 6,248,089 B1 | 6/2001 | Porat | 604/17 |
| 6,302,861 B2 | 10/2001 | Tweddell et al. | 604/15 |
| 6,358,223 B1 | 3/2002 | Mackay et al. | 604/15 |
| 6,361,601 B1 * | 3/2002 | Schulz | 118/70 |
| 6,368,539 B1 * | 4/2002 | Greenfield et al. | 264/284 |
| 6,450,986 B1 * | 9/2002 | Binner et al. | 604/15 |
| 6,511,452 B1 | 1/2003 | Rejai et al. | 604/15 |
| 6,830,554 B2 | 12/2004 | Jackson et al. | 604/11 |
| 7,066,870 B2 * | 6/2006 | Fedyk et al. | 493/156 |
| 2001/0014784 A1 | 8/2001 | Tweddell et al. | |
| 2001/0049487 A1 | 12/2001 | Buzot | |
| 2002/0177801 A1 | 11/2002 | Jackson et al. | |
| 2002/0188283 A1 * | 12/2002 | Binner et al. | 604/904 |
| 2003/0236161 A1 * | 12/2003 | Fedyk et al. | 493/480 |
| 2003/0236485 A1 * | 12/2003 | Fedyk et al. | 604/11 |
| 2004/0010220 A1 * | 1/2004 | Miller et al. | 604/15 |
| 2004/0199101 A1 * | 10/2004 | LeMay et al. | 604/11 |
| 2007/0204754 A1 * | 9/2007 | Hook et al. | 101/6 |

FOREIGN PATENT DOCUMENTS

| | | |
|---|---|---|
| GB | 2166656 | 5/1986 |

OTHER PUBLICATIONS

Canadian Office Action dated Aug. 2, 2010 from corresponding Application No. 2,608,673.

* cited by examiner

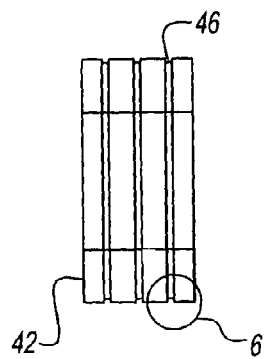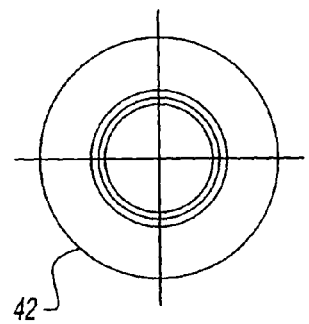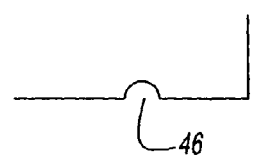
Fig. 4    Fig. 5    Fig. 6
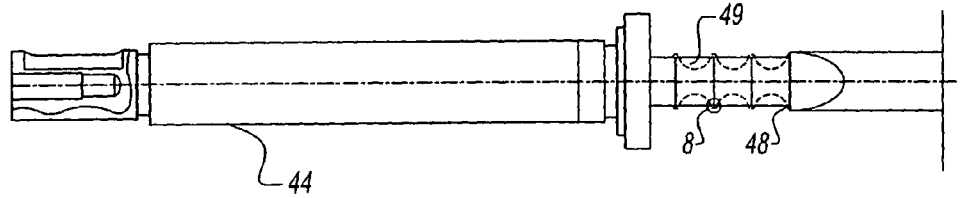
Fig. 7
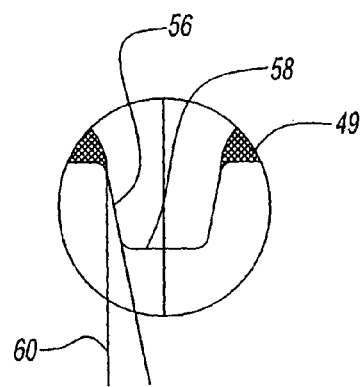
Fig. 8

TAMPON APPLICATOR BARRELS HAVING GRIPPING STRUCTURES AND METHODS OF FORMING

CROSS REFERENCE TO RELATED APPLICATIONS

This application is a division of U.S. application Ser. No. 10/870,276, filed Jun. 17, 2004, now U.S. Pat. No. 7,798,986 that claims the benefit of U.S. Provisional Application Ser. No. 60/480,559, filed Jun. 20, 2003 and U.S. Provisional Application Ser. No. 60/484,375, filed Jul. 2, 2003, the contents of each of which are incorporated by reference herein.

BACKGROUND OF THE INVENTION

1. Field of the Invention

The present invention relates to tampon applicators. More particularly, the present invention relates to tampon applicator barrels having gripping structures and methods of forming.

2. Description of Related Art

A tampon assembly is used to inject an absorbent or hygienic material, known as a tampon pledget, into the vaginal vault. The pledget of commercial tampon assemblies is typically positioned in a tampon applicator. Tampon applicators typically include a barrel and a plunger.

The pledget is housed in the barrel for expulsion therefrom through the action of the plunger. During use, an end of the barrel is inserted into the vaginal vault. Once the end of the barrel has been inserted, the plunger can be used to expel the pledget from the end of the barrel into the vaginal vault. Once the pledget is in position, the pledget expands upon contact with moisture to conform to contours of the body and, thus, provide leakage protection.

Comfort to the user during insertion of the barrel and expulsion of the pledget is an important aspect for the commercial success of the tampon assembly. The ease with which the barrel can be gripped by the user during insertion of the applicator and/or expulsion of the pledget can increase the comfort associated with the use of the tampon assembly.

Tampon applicators (e.g., barrels and/or plungers) can be made from a variety of materials. For example, tampon applicators have traditionally been made of polymers or cardboard. During the molding of polymer-based applicators, gripping structures of the desired size and shape can easily be formed.

The gripping structures on cardboard-based applicators are typically formed after the cardboard has been formed into a tube-like shape. Various gripping structure configurations for cardboard applicator barrels have been proposed to facilitate gripping of the applicator and/or expulsion of the pledget. One approach is to emboss a raised portion into the barrel, where the raised portion can take the form of a series of raised circumferential rings or a series of discrete raised areas aligned in several circumferential rows.

However, there is a continuing need for tampon applicator barrels having gripping structures that increase the user's ability to grip the applicator and methods of forming such barrels.

BRIEF SUMMARY OF THE INVENTION

It is an object of the present invention to provide tampon applicator barrels having gripping structures and methods of forming.

It is another object to provide cardboard applicator barrels having gripping rings and methods of forming.

It is another object to provide methods of defining such gripping structures having a selected height without piercing through the outermost layer of the cardboard applicator barrel.

These and other objects and advantages of the present invention are provided by compressing a barrel between a free-spinning pliable pressure wheel and a rotating mandrel to form the raised gripping structures on the barrel.

These and other objects and advantages are also provided by controlling the number of rotations of a mandrel.

These and other objects and advantages are also provided by controlling a rate of travel of a pressure wheel into a barrel with respect to a number of rotations of a mandrel.

Further objects and advantages are provided by shaping a number of protrusions on a mandrel with a pair of sloped sides and a flat top portion to control, limit, or mitigate (hereinafter "mitigate") instances of "pierce through".

Still further objects and advantages are provided by a method that controls the hardness (e.g., durometer) of a pressure wheel, the speed of descent of the pressure wheel with respect to the number of rotations of a mandrel, the shape of protrusions on the mandrel, and any combinations thereof to provide gripping structures having a desired height while mitigating instances of piercing through the applicator barrel.

Other objects and advantages are provided by a gripping structure having hairline separations formed therein and methods of forming.

In one embodiment of the present invention, a tampon applicator barrel is provided. The barrel includes a cardboard tube having a first end and a second end and at least one gripping structure being defined from the cardboard tube proximate the second end. The cardboard tube has a wall thickness of between about 0.015 and about 0.020 inches, while the gripping structure has a height of up to about 0.035 inches.

In another embodiment of the present invention, a tampon applicator barrel having a cardboard tube, a circumferential ring, and an epoxy coating is provided. The circumferential ring is defined from the cardboard tube. The epoxy coating being disposed on the cardboard tube. Then hairline separations are defined in the cardboard tube and/or the epoxy coating to provide a rough surface to at least the circumferential ring.

A method of forming a cardboard tampon applicator barrel is also provided. The method includes: moving a mandrel having a selected number of protrusions into contact with an inner surface of the tampon applicator barrel; moving a pressure wheel having a corresponding number of recesses into contact with an outer surface of the tampon applicator barrel so that the protrusions and recesses are opposite one another; and rotating at least one of the mandrel and the pressure wheel a desired number of revolutions while moving the mandrel and the pressure wheel toward one another a distance equal to or greater than a desired gripping structure height.

In addition, a method of forming a cardboard tampon applicator barrel is provided that includes: defining a mandrel having a selected number of protrusions depending therefrom; defining pressure wheel having a corresponding number of recesses defined therein, the pressure wheel having a Type A durometer in a range preferably between about 45 and about 95; then, moving the selected number of protrusions into contact with an inner surface of the tampon applicator barrel; moving the corresponding number of recesses into contact with an outer surface of the tampon applicator barrel so that the protrusions and recesses are opposite one another;

and rotating at least one of the mandrel and the pressure wheel a desired number of revolutions while moving the mandrel and the pressure wheel toward one another a distance equal to or greater than a desired gripping structure height.

The above-described and other features and advantages of the present invention will be appreciated and understood by those skilled in the art from the following detailed description and drawings.

BRIEF DESCRIPTION OF THE SEVERAL VIEWS OF THE DRAWINGS

FIG. 4 is a side view of an exemplary embodiment of a pressure wheel;

FIG. 5 is an end view of the pressure wheel of FIG. 4;

FIG. 6 is an enlarged view of circle 6 of FIG. 4;

FIG. 7 is a side view of an exemplary embodiment of the mandrel of FIG. 4;

FIG. 8 is an enlarged view of circle 8 of FIG. 7;

DETAILED DESCRIPTION OF THE INVENTION

Figure 1:
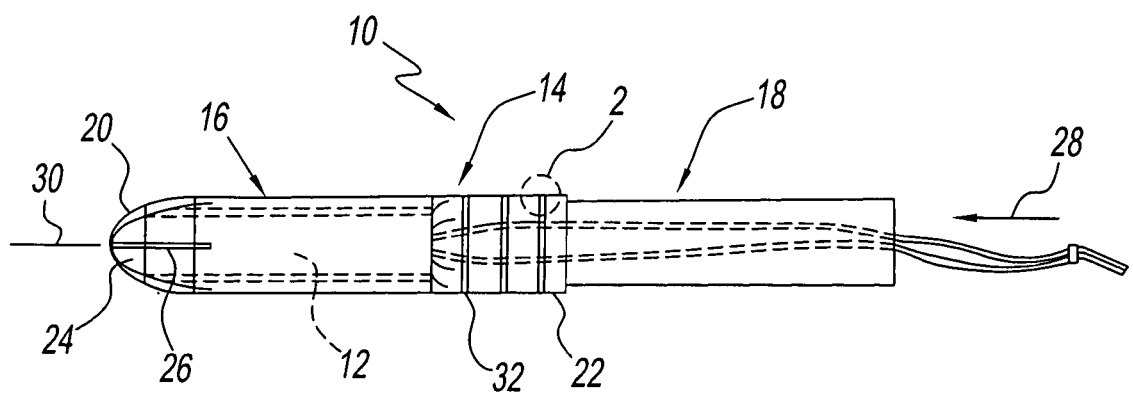
FIG. 1 is a side view of an exemplary embodiment of a tampon assembly.
Figure 2:
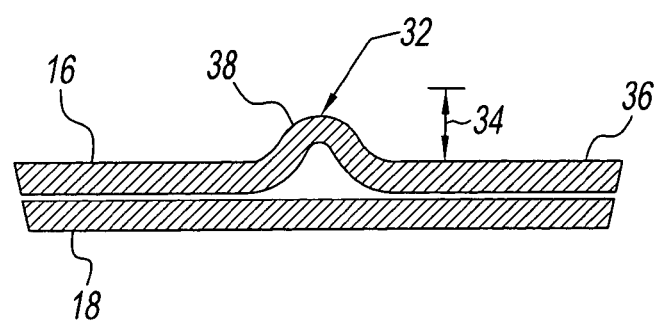
FIG. 2 is an enlarged sectional view of circle 2 of FIG. 1 illustrating an exemplary embodiment of a gripping structure.

Referring to the drawings and in particular to FIGS. 1 and 2, a tampon assembly generally represented by reference numeral 10 according to the present invention is shown. Assembly 10 has a pledget 12 and an applicator 14. Applicator 14 includes a barrel 16 and a plunger 18.

Barrel 16 has a generally tubular shape having has a first end 20 and a second end 22. First end 20 defines the insertion end of barrel 16 and includes a number or a plurality of petals 24. Petals 24 are defined in first end 20 by a number or plurality of slits 26. Barrel 16 is illustrated by way of example as including six petals 24. Of course, it is contemplated by the present invention for barrel 16 to have more or less than six petals. For example, barrel 16 can have any number of petals between about two and eight petals, such as, for example, three, four, five or six petals.

Plunger 18 can expel pledget 12 from barrel 16. Plunger 18 is positioned to slide in barrel 16 at second end 22. Pledget 12 is expelled through first end 20 through the movement of plunger 18 in the direction of arrow 28, which is parallel to a longitudinal axis 30 of barrel 16. As plunger 18 moves in the direction of arrow 28, the plunger can urge pledget 12 into petals 24 until the petals open along slits 26 and the pledget is expelled from barrel 16 through first end 20.

Barrel 16 preferably includes one or more layers of cardboard. The layer(s) of barrel 16 can be convolutedly or spirally wound as is known in the art. Alternately, the layer(s) of barrel 16 can be rolled. Of course, barrel 16 can be formed of any combination of convolute and/or rolled cardboard layers.

As used herein, the term "cardboard" shall include materials such as, but not limited to, cardboard, paper, paper or cardboard laminate, paper slurry, pulp slurry, pulp-molded paper, or any combinations thereof.

Barrel 16 preferably has a wall thickness of between about 0.008 inches and about 0.020 inches, more preferably at least about 0.011 inches, with between about 0.015 and about 0.020 inches being most preferred.

In some embodiments of the present invention, barrel 16 includes one or more coatings and/or polymer film layers or laminates (not shown) disposed thereon. For example, barrel 16 can include an epoxy coating as set forth in commonly owned and assigned U.S. Pat. No. 5,931,803 to Jackson, the contents of which are incorporated herein by reference thereto.

In order to assist the user in gripping barrel 16, second end 22 includes one or more gripping structures 32 defined thereon. Gripping structures 32 are raised portions of barrel 16 that facilitate control of the barrel. Specifically, gripping structures 32 have a height 34 that imparts a selected gripability to barrel 16.

Height 34 is defined as the distance from an outside surface 36 of barrel 16 to a top or apex 38 of gripping structure 32. For example, height 34 can be up to about 0.035 inches, preferably between about 0.012 and about 0.030 inches, and most preferably between about 0.015 and about 0.024 inches. Thus, height 34 provides gripping structure 32 with a pronounced ring-like shape.

Barrel 16 is illustrated by way of example as having three evenly spaced, circumferential (e.g., generally perpendicular to axis 30) gripping structures 32. In addition, gripping structures 32 are illustrated by way of example as being continuous about the circumference of barrel 16. However, it is contemplated for barrel 16 to have more or less than three gripping structures 32, for the gripping structures to be discontinuous about the circumference of the barrel, for the gripping structures to be unevenly spaced, and any combinations thereof.

Figure 3:
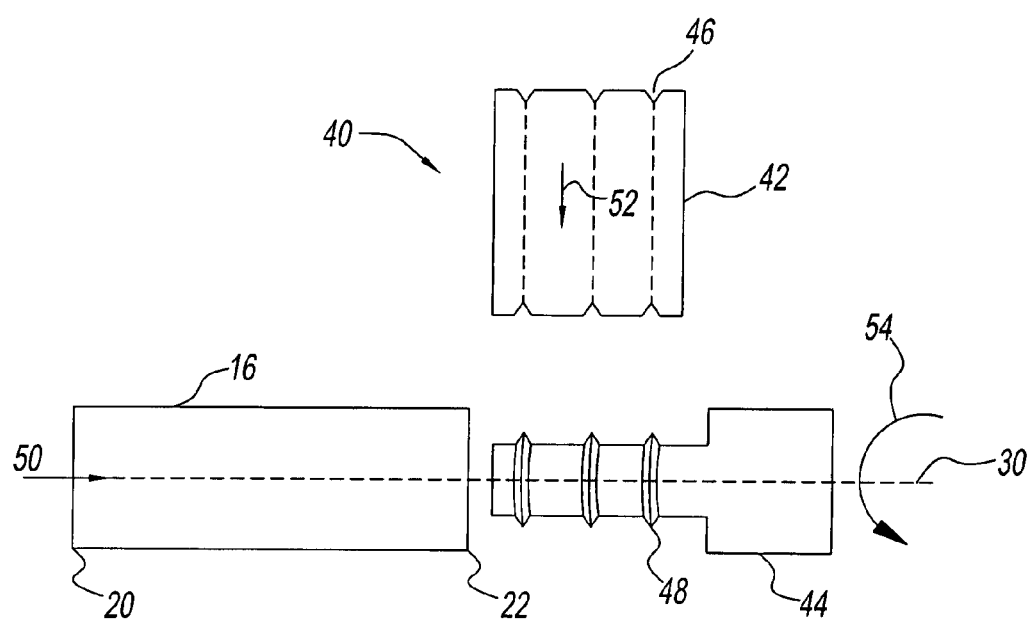
FIG. 3 is a schematic depiction of an exemplary embodiment of a method of forming the gripping structure of FIG. 2.

In the past, gripping structures 32 having height 34 in the aforementioned ranges have been difficult, if not impossible, to achieve without piercing through outer surface 36 of barrel 16. Advantageously, it has been determined that gripping structures 32 having height 34 can be formed using a method 40 illustrated in FIG. 3 without the pierce through of prior methods. For purposes of clarity, various components (e.g., petals 24, slits 26, etc.) of barrel 16 are omitted from FIG. 3.

Method 40 uses a pressure wheel 42 and a mandrel 44 to form structures 32. Pressure wheel 42 is illustrated in FIGS. 4 through 6, while mandrel 44 is illustrated in FIGS. 7 and 8.

Pressure wheel 42 has a number of recesses 46 defined in its outer circumference, and mandrel 44 has a corresponding number of protrusions 48 defined in its outer circumference. The number of recesses 46 and protrusions 48 correspond to the number of desired gripping structures 32.

Mandrel 44 and barrel 16 are moved into contact with one another in a first direction 50 that is parallel to axis 30. For example, mandrel 44 can inserted into second end 22 of barrel 16, the second end can be moved over the mandrel, or any combinations thereof. In this position, mandrel 44 is positioned in barrel 16 so that protrusions 48 are in contact with the barrel.

Next, pressure wheel 42 is moved into contact with outside surface 36 of barrel 16 in a second direction 52 that is perpendicular to axis 30. In this position, indentations 46 are positioned opposite protrusions 48.

Once pressure wheel 42 is in contact with barrel 16, mandrel 44 is rotated in a third direction 54, which is generally parallel to axis 30. While mandrel 44 is being rotated, pressure wheel 42 is moved along second direction 52 a distance substantially equal or greater to height 34. In this manner, indentations 46 and protrusions 48 are compressed together about barrel 16, while the barrel is rotated eccentrically by mandrel 44 to form gripping structures 32 in the barrel.

It should be recognized that method 40 is described by way of example as rotating mandrel 44. Of course, it is contemplated that pressure wheel 42 can be the driving member, barrel 16 can the driving member, or any combinations thereof. It should also be recognized that method 40 is described by way of example as moving rotating pressure wheel 42 in second direction 52. Of course, mandrel 44 and barrel 16 can be moved in a direction opposite second direction 52.

Advantageously, pressure wheel 44 is formed of a materials of various hardness and frictional properties to mitigate instances of "pierce through" of outer surface 36 during formation of gripping structures 32. It believed that using pliable pressure wheel 44 reduces the sheer on barrel 16 as it is being formed by the pressure wheel and mandrel 44. In one embodiment, pressure wheel 44 is formed of a pliable material having a Type A durometer in a range preferably between about 45 and about 95 as measured by ASTM D2240, more preferably between about 55 and about 85, and most preferably about 85 on the absolute scale. For example, pressure wheel 44 can be formed of urethane, rubber, plastics, and other materials in the aforementioned durometer ranges.

It has also been determined that the rate of travel of pressure wheel 42 in direction 52 with respect to the rotation of mandrel 44 in direction 54 can mitigate instances of "pierce through". Namely, it has been determined that sheer forces on barrel 16 can be reduced by moving pressure wheel 42 in direction 52 while mandrel 44 is rotated a selected number of rotations in direction 54. For example, mandrel 44 can be rotated in third direction 54 between about four (4) and about twenty (20), and preferably between about eight (8) and about twelve (12) revolutions, while pressure wheel 42 is moved height 34 in second direction 52. Thus, method 40 can control the number of revolutions of mandrel 42 with respect to the speed of travel of pliable pressure wheel 44 in second direction 52 to mitigate instances of "pierce through".

Pressure wheel 42 can be moved in second direction 52 at the desired rate with a cam, a pneumatic cylinder, a hydraulic cylinder, a linear motor, or other components.

In addition, method 40 can control the shape of protrusions 48 on mandrel 44 to mitigate instances of "pierce through". For example in one embodiment, protrusions 48 on mandrel 44 can have a pair of sloped sides 56 and a top portion 58. Sides 56 are sloped with respect to a plane 60 in a range of about 7.5 degrees to about 11.5 degrees, preferably about 9.5 degrees. In this example, plane 60 is perpendicular to axis 30. Top portion 58 is, preferably, flat. Namely, top portion is preferably parallel to axis 30.

In another embodiment, mandrel 44 can include pliable regions 49 positioned adjacent protrusions 48. Pliable regions 49, preferably, are undercut portions of mandrel 44 adjacent to sloped sides 56 protrusions 48, where the undercut regions are filled with pliable material. It has been determined that pliable regions 49 can also reduce the sheer on barrel 16 as it is being formed by pressure wheel 42 and mandrel 44. In one embodiment, the pliable material of pliable regions 49 have a Type A durometer in a range preferably between about 45 and about 95 as measured by ASTM D2240, more preferably between about 55 and about 85, and most preferably about 85 on the absolute scale. For example, regions 49 can be formed of urethane, rubber, plastics, and other materials in the aforementioned durometer ranges.

It has been found that the combination of gently sloped sides 56, flat top portion 58, and/or regions 49 can aid method 40 in mitigating instances of "pierce through".

It should be recognized that protrusions 48 are illustrated by way of example only as semi-circular. Of course, it is contemplated by the present disclosure for protrusions 48 to have other shapes, such as, but not limited to polygonal, ovoid, circular, or any combinations thereof.

Accordingly, method 40 can control the hardness of pressure wheel 42, the speed of descent of the pressure wheel with respect to the number of rotations of mandrel 44, the shape of protrusions 48 on the mandrel, and any combinations thereof, to provide gripping structures 32 having the desired height 34 while mitigating the instances of piercing through barrel 16.

Figure 9:
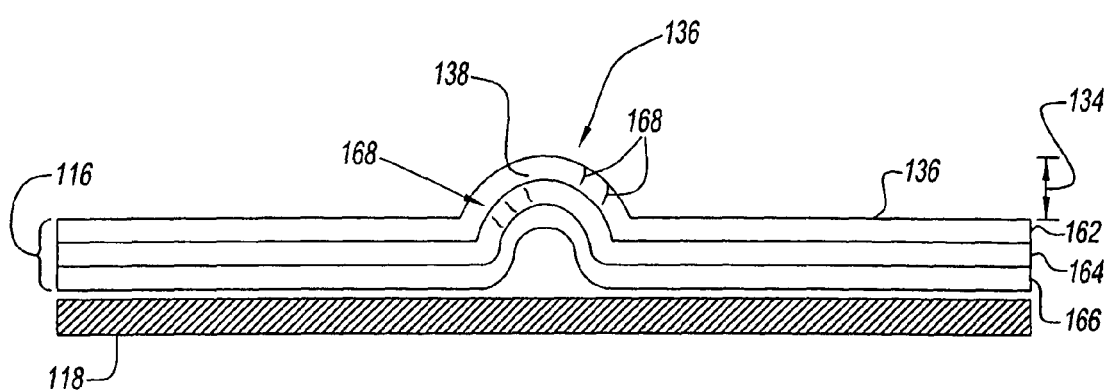
FIG. 9 is an alternate exemplary embodiment of the gripping structure of FIG. 2.

Referring now to FIG. 9, an alternate embodiment of a gripping structure 132 is illustrated. Here, component parts performing similar and or analogous functions are numbered in multiples of one hundred.

Gripping structure 132 is defined in barrel 116 having plunger 118 slidably disposed therein. Barrel 116 include a coating 162 disposed on an outer layer or laminate 164. In addition, barrel 116 can include one or more inner layers or laminates 166 (only one shown). For example, coating can be an epoxy coating as set forth in commonly owned and assigned U.S. Pat. No. 5,931,803 to Jackson.

Gripping structure 132 has a height 134 that is defined as the distance from an outside surface 136 of barrel 116 to a top or apex 138 of the gripping structure. For example, height 134 can be up to about 0.035 inches, preferably between about 0.012 and about 0.030 inches, and most preferably between about 0.015 and about 0.024 inches.

It has been determined that controlling the process conditions used during manufacture of gripping structure 132 can cause one or more micro or hairline separations 168 in coating 162 and/or outer layer 164. Separations 168 can provide gripping structure 132 with a rough surface that can supplement the gripping benefit of the gripping structures themselves. However, separations 168 terminate prior to actually extending entirely through outer layer 164, or only slightly pierce through the outer layer.

In one embodiment, separations 168 can be formed in coating 162 and provide edges (not shown) that directly contact the user's finger (not shown) to enhance the gripability of gripping structures 132.

In an alternate embodiment, separations 168 can be formed in outer layer 164. Here, coating 162 has a thickness sufficient to allow the edges of separations 168 to be felt through the coating and, thus, provide enhanced gripability to gripping structures 132.

In yet another embodiment, separations 168 can be formed in both coating 162 and outer layer 164 to provide both direct and indirect edges to enhanced gripability of gripping structures 132.

For example, it has been found that the moisture content of coating 162 and/or layers 164, 166 can be controlled during creation of the gripping structures 132 to cause formation of separations 168. In addition, other process conditions in addition to or in lieu of moisture content can be controlled during manufacture of gripping structure 132 to form separations 168. For example, process conditions such as, but not limited to, the hardness (e.g., durometer) of a pressure wheel, the speed of descent of the pressure wheel with respect to the number of rotations of a mandrel, the shape of protrusions on the mandrel, thickness and/or composition of coating 162, thickness and/or composition of layer 164 and/or 166, or any combinations thereof.

It should also be noted that the terms "first", "second", "third", "upper", "lower", and the like may be used herein to modify various elements. These modifiers do not imply a spatial, sequential, or hierarchical order to the modified elements unless specifically stated.

While the present invention has been described with reference to one or more exemplary embodiments, it will be understood by those skilled in the art that various changes may be made and equivalents may be substituted for elements thereof without departing from the scope of the present invention. In addition, many modifications may be made to adapt a particular situation or material to the teachings of the disclosure without departing from the scope thereof. Therefore, it is intended that the present invention not be limited to the particular embodiment(s) disclosed as the best mode contemplated for carrying out this invention, but that the invention will include all embodiments falling within the scope of the present disclosure.

What is claimed is:

1. A method of forming a cardboard tampon applicator barrel, comprising:
    moving a mandrel having a selected number of protrusions into contact with an inner surface of the tampon applicator barrel;
    defining a pliable region in said mandrel adjacent to each of said selected number of protrusions, said selected number of protrusions being a different material than said pliable region;
    moving a pressure wheel having a corresponding number of recesses into contact with an outer surface of the tampon applicator barrel so that said protrusions and recesses are opposite one another; and
    rotating at least one of said mandrel and said pressure wheel a desired number of revolutions while simultaneously moving said mandrel and said pressure wheel toward one another a distance equal to or greater than a desired gripping structure height.

2. The method as in claim 1, wherein said desired number of revolutions comprises between about four and about twenty revolutions.

3. The method as in claim 2, wherein said desired number of revolutions comprises between about eight and about twelve revolutions.

4. The method as in claim 1, wherein said pressure wheel has a Type A durometer in a range preferably between about 45 and about 95.

5. The method as in claim 4, wherein said durometer is between about 55 and about 85.

6. The method as in claim 4, wherein said durometer is 85.

7. The method as in claim 1, wherein defining said pliable region comprises undercutting a portion of said mandrel adjacent to each of said selected number of protrusions and filling said portion with pliable material having a Type A durometer in a range between about 45 and about 95.

8. The method as in claim 1, wherein said rotating comprises rotating said mandrel said desired number of revolutions while simultaneously moving said mandrel and said pressure wheel toward one another said distance equal to or greater than said desired gripping structure height thereby compressing said selected number of protrusions and said corresponding number of recesses together about the cardboard tampon applicator barrel forming at least one raised gripping structure in the cardboard tampon applicator barrel, and wherein said rotation of said mandrel drives said pressure wheel to rotate.

9. The method as in claim 1, wherein said selected number of protrusions each have a pair of sloped sides and a flat top portion therebetween.

10. The method as in claim 1, wherein said selected number of protrusions includes at least one protrusion that extends about a circumference on an outer surface of said mandrel, wherein said corresponding number of recesses includes at least one recess that extends about a circumference on an outer surface of said pressure wheel, and wherein rotating at least one of said mandrel and said pressure wheel said desired number of revolutions while simultaneously moving said mandrel and said pressure wheel toward one another said distance equal to or greater than said desired gripping structure height thereby compresses said at least one protrusion and said at least one recess together about the cardboard tampon applicator barrel forming at least one raised gripping structure in the cardboard tampon applicator barrel having a ring shape that is continuous about a circumference of the cardboard tampon applicator barrel.

11. A method of forming a cardboard tampon applicator barrel, comprising:
    moving a mandrel having a selected number of protrusions into contact with an inner surface of the tampon applicator barrel;
    moving a pressure wheel having a corresponding number of recesses into contact with an outer surface of the tampon applicator barrel so that said protrusions and recesses are opposite one another; and
    rotating at least one of said mandrel and said pressure wheel a desired number of revolutions while simultaneously moving said mandrel and said pressure wheel toward one another a distance equal to or greater than a desired gripping structure height,
    wherein defining said mandrel comprises defining each of said selected number of protrusions with a pair of sides and a top, said pair of sides being sloped with respect to a plane perpendicular to the longitudinal axis of the mandrel in a range of about 7.5 degrees to about 11.5 degrees.

12. A method of forming a cardboard tampon applicator barrel, comprising:
    defining a mandrel having a selected number of protrusions depending therefrom;
    defining pressure wheel having a corresponding number of recesses defined therein, said pressure wheel having a Type A durometer in a range between about 45 and about 95;
    moving said selected number of protrusions into contact with an inner surface of the tampon applicator barrel;
    moving said corresponding number of recesses into contact with an outer surface of the tampon applicator barrel so that said protrusions and recesses are opposite one another; and
    rotating at least one of said mandrel and said pressure wheel a desired number of revolutions while simultaneously moving said mandrel and said pressure wheel toward one another a distance equal to or greater than a desired gripping structure height,
    wherein defining said mandrel comprises defining each of said selected number of protrusions with a pair of sides and a top, said pair of sides being sloped with respect to a plane perpendicular to the longitudinal axis of the mandrel in a range of about 7.5 degrees to about 11.5 degrees.

13. The method as in claim 12, wherein said durometer is between about 55 and about 85.

14. The method as in claim 13, wherein said durometer is 85.

15. The method as in claim 12, further comprising defining a pliable region in said mandrel adjacent to each of said selected number of protrusions.

16. The method as in claim 15, wherein defining said pliable region comprises undercutting a portion of said mandrel adjacent to each of said selected number of protrusions and filling said portion with pliable material having a Type A durometer in a range between about 45 and about 95.

17. The method as in claim 12, wherein said desired number of revolutions comprises between about four and about twenty revolutions.

18. The method as in claim 17, wherein said desired number of revolutions comprises between about eight and about twelve revolutions.

* * * * *